(12) United States Patent
Zahn et al.

(10) Patent No.: US 9,234,883 B2
(45) Date of Patent: Jan. 12, 2016

(54) APPARATUS AND METHOD FOR ANALYZING SAMPLE FLUIDS

(75) Inventors: Dorothea Zahn, Dresden (DE); Frank Bier, Potsdam (DE)

(73) Assignee: BST Bio Sensor Technology GmbH, Berlin (DE)

(*) Notice: Subject to any disclaimer, the term of this patent is extended or adjusted under 35 U.S.C. 154(b) by 92 days.

(21) Appl. No.: 14/003,631

(22) PCT Filed: Mar. 5, 2012

(86) PCT No.: PCT/EP2012/053762
§ 371 (c)(1),
(2), (4) Date: Nov. 12, 2013

(87) PCT Pub. No.: WO2012/119992
PCT Pub. Date: Sep. 13, 2012

(65) Prior Publication Data
US 2014/0057359 A1 Feb. 27, 2014

(30) Foreign Application Priority Data
Mar. 8, 2011 (DE) .................... 10 2011 005 254

(51) Int. Cl.
*G01N 33/49* (2006.01)
*G01N 33/66* (2006.01)
(Continued)

(52) U.S. Cl.
CPC ............ *G01N 33/49* (2013.01); *G01N 33/4875* (2013.01); *Y10T 436/110833* (2015.01); *Y10T 436/144444* (2015.01)

(58) Field of Classification Search
CPC ... G01N 33/48; G01N 33/49; G01N 33/4875; Y10T 436/144444; Y10T 436/104998; Y10T 436/110833; Y10T 436/25; Y10T 436/2575
USPC .................. 436/14, 43, 44, 63, 95, 174, 180; 435/14; 422/63, 66, 68.1, 501, 509, 422/510, 512, 554
See application file for complete search history.

(56) References Cited

U.S. PATENT DOCUMENTS 3,526,480 A 9/1970 Reid et al.
5,077,010 A * 12/1991 Ishizaka et al. ............... 422/408
(Continued)

FOREIGN PATENT DOCUMENTS

DE 1648865 C3 7/1974
DE 102004050062 A1 4/2006
(Continued)

OTHER PUBLICATIONS

International Search Report from PCT/EP2012/053762 mailed Jul. 5, 2012.
(Continued)

*Primary Examiner* — Maureen Wallenhorst
(74) *Attorney, Agent, or Firm* — Novak Druce Connolly Bove + Quigg LLP

(57) ABSTRACT

The invention relates to an apparatus and a method for analyzing sample fluids, in particular for analyzing blood samples, for example for the purpose of determining the glucose content, with the same apparatus. A cavity delimited by a carrier tape is hereby positioned above a sensor surface, sample fluid is received in the cavity, at least one value of the sample fluid is measured, the cavity containing the sample fluid is removed from the sensor surface, and a regeneration agent is supplied to the sensor surface by way of the carrier tape.

12 Claims, 2 Drawing Sheets

Figure 1:
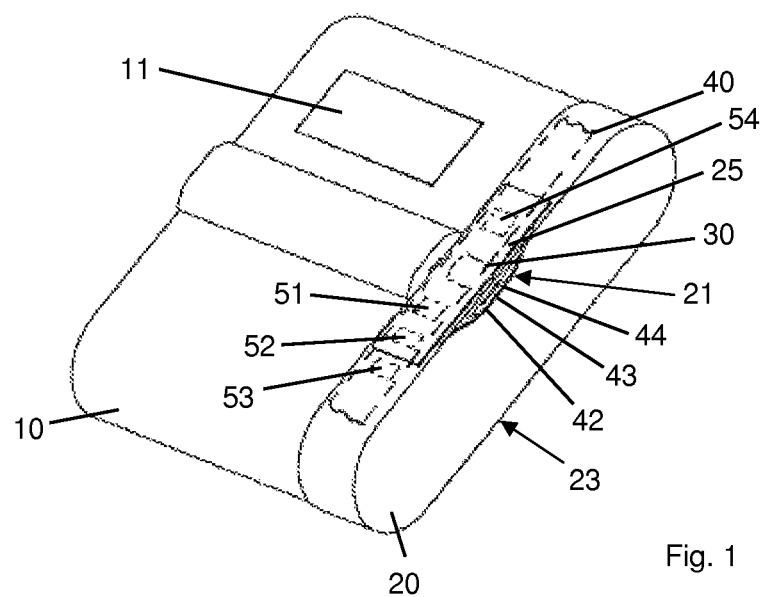

(51) Int. Cl.
*G01N 35/04* (2006.01)
*G01N 33/487* (2006.01)

(56) References Cited

U.S. PATENT DOCUMENTS

| | | | |
|---|---|---|---|
| 6,988,996 | B2 | 1/2006 | Roe et al. |
| 7,378,270 | B2 * | 5/2008 | Azarnia et al. ............. 435/287.2 |
| 2002/0188224 | A1 * | 12/2002 | Roe et al. ...................... 600/584 |
| 2003/0211616 | A1 * | 11/2003 | Leong ............................... 436/8 |
| 2005/0230253 | A1 | 10/2005 | Marquant |
| 2006/0173380 | A1 * | 8/2006 | Hoenes et al. ................. 600/583 |
| 2006/0216817 | A1 * | 9/2006 | Hoenes et al. ............. 435/287.2 |
| 2007/0217950 | A1 * | 9/2007 | Kramer et al. .................. 422/66 |
| 2012/0004852 | A1 * | 1/2012 | Miltner et al. .................. 702/19 |
| 2012/0045842 | A1 * | 2/2012 | Petrich et al. ................... 436/95 |

FOREIGN PATENT DOCUMENTS

| | | |
|---|---|---|
| EP | 1247092 A1 | 10/2002 |
| WO | 2005032372 A1 | 4/2005 |
| WO | 2005047861 A2 | 5/2005 |

OTHER PUBLICATIONS

D. Zahn et al.: "Novel device for quick measurement of glucose in POCT areas without pre-analytical steps based on a multi-way glucose biosensor", Eng. Life Sci. 2009, 9, No. 5, pp. 398-403.

* cited by examiner

APPARATUS AND METHOD FOR ANALYZING SAMPLE FLUIDS

CROSS-REFERENCE TO RELATED APPLICATIONS

This application is a §371 national stage entry of International Application No. PCT/EP2012/053762, filed Mar. 5, 2012, which claims priority to German Application No. 10 2011 005 254.2, filed Mar. 8, 2011, which are hereby incorporated herein by reference in their entireties.

The present invention relates to an apparatus and a method for analyzing sample fluids, in particular for analyzing blood samples, for example for determining the glucose level by using the same apparatus.

The so-called Point-of-Care testing (on-site diagnosis) is considered increasingly important in the field of biochemical analysis and especially in medical in vitro diagnostics because doctor and patient equally benefit from a patient-centered diagnosis. Today's developments are directed to tests that can be performed by the patients themselves, such as the glucose self-test.

By using the evolving telemedicine, therapeutic consequences can be initiated more quickly, especially when a safe quality can be ensured in the patient-centered analysis.

However, like the reusable biosensors used in the laboratory, which can be calibrated and controlled and thus allow a verifiable quality, cannot be used for patient self-monitoring and self-diagnosis, since the regeneration of the biosensors after a measurement is a process that could hitherto not be converted into a patient-acceptable form.

Today, only disposable items in the form of strips, disposable sensors or disposable cuvettes are used to perform on-site diagnostics for patient self-monitoring. Due to the basic technology (the required chemistry must dissolve in the sample when this sample applied), these articles can only be used once.

In a control measurement, a single-use sensor/single-use strip/single-use cuvette is provided with a control solution specified by the manufacturer, and then measured. Regardless of whether the result is correct or false, the single-use items must then be discarded and a new single-use sensor/single-use strip/single-use cuvette must be used in each case for a patient measurement.

A mobile measuring system operating on the basis of a reusable biosensor already exists for the professional point-of-care application, as disclosed in EP 1247092 B1. The fluidic system for cleaning is based on a macrofluidic mechanism with a pump and a valve, wherein the cleaning solutions are pumped from a reservoir across the sensor. A disadvantage of this embodiment is that the sample quantity must not be less than a specified volume and that a relatively large volume of cleaning solution must be available. Furthermore, such a measurement system does not seem suitable for patient self-monitoring due to its complexity and the associated susceptibility to malfunctions.

Furthermore, an apparatus and a method for receiving and analyzing or manipulating sample fluids on a microfluidic platform is known from DE 10 2004 050 062 A1, wherein the fluid sample is supplied to the platform, a measurement or analysis of the sample is carried out, and the platform is thereafter separated from a carrier and discarded. This apparatus and the method carried out with this apparatus can advantageously be easily operated by the patient, as the patient must only supply the fluid sample to this platform, e.g. in the form of a drop of blood from his finger. All additional operations, such as the measurement and separation and disposal of the platform can be done automatically. This allows a mobile use of the presented apparatus. However, this must be weighed against the disadvantages of the need to dispose of the separated platforms as well as the risk of contamination of the apparatus for measuring specific values of the fluid sample, because the sample must be retained in the vicinity of the platform designated to receive the next fluid sample over a long period until the next measurement, which may falsify the next test results. As stated above, however, a reliable measurement is essential especially in measurements to be performed by patients themselves.

It is therefore the object of the invention to provide an apparatus and a method for testing sample fluids, with which the measurement and/or analysis of samples, especially sample fluids, can be implemented in a simple, reliable, cost-effective, self-explanatory, hygienic and low maintenance manner.

This object is attained with the inventive apparatus for testing sample fluids according to claim 1 and with the inventive method for testing sample fluids according to claim 9. Advantageous embodiments of the inventive apparatus are recited in the dependent claims 2 through 8. Advantageous embodiments of the inventive method are recited in the dependent claims 10 through 15.

The inventive apparatus for analyzing sample fluids includes a sensor for measuring at least one value of the sample fluid, wherein the sensor has a sensor surface configured to perform the measurement. Furthermore, the inventive apparatus includes a carrier tape by which, in cooperation with the sensor surface, at least one measuring cell for receiving sample fluid is formed or can be formed. According to the invention, at least one regeneration agent for regenerating the sensor is contained on or in the carrier tape, wherein the carrier tape is configured such that the regeneration agent can be applied to the sensor surface. In particular, the glucose content in a blood sample can be determined with the apparatus according to the invention, meaning that diabetic patients can easily determine the blood sugar with the inventive apparatus. This is performed by the sensor of the apparatus, which is a measuring apparatus with a surface that may optionally be part of a housing of the measuring apparatus. Measuring processes or analysis processes, such as an optical measurement, can be implemented via the surface of the sensor. To this end, a fluid sample located on the sensor surface in the measuring cell is measured and analyzed. This measuring cell is delimited on one side by a section of the carrier tape and on the other side of the sensor surface. Here, the term carrier tape is not limited to only a flexible tape, but may within the context of the invention also be a rigid planar body, a sections of which delimits the measuring cell on one side. The geometric dimensions of the carrier tape are irrelevant, so that optionally a plate-like plane can be used as a carrier tape. The inventive apparatus is preferably also configured for repeated measurements, wherein the carrier tape together with the sensor surface temporarily forms a plurality of measuring cells, e.g. sequentially depending on the respective position of individual sections above the carrier tape above the sensor surface. Stated differently, different sections of the carrier tape can be positioned on the sensor surface in each case by moving the carrier tape, thus temporarily forming different sensors. The sensor are regenerated after each measurement process so as to make the sensor again ready for use, and/or to obtain again correct results in a next measurement. A regeneration agent is placed on the sensor surface for regeneration when the section of the carrier tape containing the regeneration agent is superimposed on the sensor surface.

With the apparatus according to the invention, major components of the apparatus, such as the sensor and the control electronics, can be used multiple times. This prevents false measurement and analysis results, because the sensor is automatically cleaned and/or regenerated after each measurement by the carrier tape and/or the regeneration agent contained in the carrier tape.

In an advantageous embodiment of the apparatus according to the invention, the respective measuring cell may be realized by the sensor surface and a cavity formed in the carrier tape for receiving the sample fluid. In other words, a pocket having a small depth, which can be partially filled with the sample fluid, may be incorporated at least in a section, and advantageously in several sections of the carrier tape. The depth is dimensioned such that capillary forces alone are sufficient to draw sample fluid into the cavity.

Alternatively, each cell can be realized by the sensor surface and a substantially flat section of the carrier tape and a lateral border of the sensor surface, thus also producing a hollow volume (void) above the sensor surface. In this embodiment, the carrier tape is constructed to be essential planar, and the sensor surface is located below the edge of a lateral border of the sensor surface, with the carrier tape, the sensor surface and the lateral border then defining a volume that can be at least partially filled with the sample fluid. Again, the depth of the volume is to be adjusted so that capillary forces can cause the volume to be at least partial filled with sample fluid.

Furthermore, the regeneration agent is preferably received in at least one void in the carrier tape. Preferably, the regeneration agent is arranged in several voids in the carrier tape, in particular arranged sequentially one after the other, and alternating with the cavity for receiving the sample fluid. In particular, a group of voids alternates in each case with a respective cavity.

To wet the sensor surface with the regeneration agent, at least one of the voids receiving a regeneration agent may advantageously incorporate a rated break point, which opens under mechanical load, allowing the regeneration agent to be released from the carrier tape. Optionally, the carrier tape may at least in a region of the void have a membrane or a film on the side facing the sensor surface with a lower mechanical strength than the rest of the carrier tape so that the membrane or the film can be destroyed in at least in one position of the void above the sensor surface and the regeneration agent can reach the sensor surface.

More particularly, a detergent and/or a calibration agent may reside in several voids forming a regeneration agent. I.e., either a detergent or a calibration agent is contained in a void, so that detergents and/or calibration agents may be contained in the totality of voids in a carrier tape that are associated with a cavity. The sensor or the sensor surface can be regenerated with the detergent and/or the calibration agent. The sensor surface is cleaned with the detergent, thus enabling an error-free optical measurement or electrochemical measurement. The sensor can be calibrated with the calibration agent.

The regeneration agent in the cavity of the carrier tape may be a detergent, such as a buffer solution, or may be a calibration agent.

The volume of the cavity is preferably between 0.1 µl and 1000 µl.

In a preferred embodiment of the apparatus according to the invention, the support tape may be an endless tape. The cavities for receiving the sample fluid and the voids containing regeneration agents are in this endless tape arranged sequentially one after the other. In an alternative embodiment, the carrier tape may be a disk. The aforementioned cavities and voids are arranged in groups, with each group being provided for a measurement or an analysis of sample fluid. The endless tape need not necessarily be arranged in only a single loop, but may extend in several loops or bends, so that a very long carrier tape having a corresponding number of cavities and voids can be accommodated in a relatively small space.

Advantageously, the apparatus may further include a positive guide for guiding the carrier tape over the sensor surface, so that the respective cavities and voids can be automatically fed to the sensor surface. A further cleaning effect on the sensor surface can be achieved by way of dynamic friction of the carrier tape on the sensor surface and optionally by way of suitable coating of the carrier tape on the side facing the sensor surface, The cavity for receiving the sample fluid or a part of the measuring cell thus produced is discarded after completion of the measurement or analysis. Accordingly, the cavity need not be cleaned. The sensor surface is regenerated with a cleaning agent and/or a calibration agent, so that a new precise measurement can be easily performed. This is a huge advantage particularly with respect to the conventional mobile analysis and measurement devices, since these disadvantageously require that either the entire measuring cell and thus also the sensor surface is discarded, or wherein automatic cleaning of the sensor is either not possible or only at a high cost or wherein there is a risk of erroneous measurements and analyses, respectively, caused by contamination of the sensor.

In particular, for an automated embodiment of the apparatus according to the invention, the apparatus may include a drive system and a positioning system for transporting and sequentially positioning the cavities for receiving the sample fluid and the voids with the regeneration agent above the sensor surface. In the above-mentioned alternative embodiment of the carrier tape, wherein the measuring cell is realized by the sensor surface and a substantially flat section of the carrier tape, and a lateral border of the sensor surface, the flat section of the carrier tape may be positioned above the sensor surface by the drive and positioning system. The drive and positioning system is preferably implemented in the form of a replaceable cartridge, on which or in which the carrier tape is slideably arranged.

In a further advantageous embodiment of the invention, the apparatus includes a pressure device for applying a mechanical pressure on a respective void containing a regeneration agent. Such pressure device may, for example, be a constriction, into which the carrier tape enters and which exerts a compressive force on a void above the sensor surface due to the resulting wedge action. Alternatively, the pressure device may also be a moving working fluid for applying pressure to the void, so that the void is opened and the regeneration agent can exit onto the sensor surface.

To facilitate the reception of the sample fluid in the cavity in the carrier tape, the cavity may be substantially open on the side facing the sensor surface for receiving the sample fluid. This opening in the bottom side extends into the lateral region of the carrier tape so that the cavity is open on the side, enabling the introduction of fluid samples, such as blood, into the cavity by capillary action. In an alternative embodiment, the cavity for receiving the sample fluid may be closed on the side facing the sensor surface, having lateral openings only on the side. The sample fluid can be received through one lateral opening and can then be supplied the other side opening, and thus to a laterally arranged sensor surface.

Moreover, the invention also provides a process for analyzing sample fluids, wherein at least one value of the sample fluid is measured and analyzed by a sensor, wherein the steps of positioning a cavity delimited by a carrier band above a sensor surface, receiving sample fluid in the cavity, measuring at least one value of the sample fluid, removing the cavity with the sample fluid from the sensor surface, supplying a regeneration agent to the sensor surface by way of the carrier tape, as well as contacting the sensor surface with the regeneration agent to regenerate the sensor are performed.

The inventive method for analyzing sample fluids is particularly suited for measuring glucose levels in blood, in particular by using the inventive apparatus. The sample fluid is received in a cavity formed by a surface of the sensor and a cavity formed in the carrier tape through capillary action. The sample fluid can be measured, for example, optically or electrochemically through the sensor surface. The measurement is not necessarily intended to determine only discrete values, but the concept of a measurement may also include an analysis for determining whether substances are present in certain concentrations or whether certain limits of physical quantities in the sample fluid are attained.

The cavity is removed from the sensor surface by moving the carrier tape. Moving the carrier tape, which is also used to supply the regeneration agent to the sensor surface, is preferably automatic and is triggered by the measurement. For analyzing sample fluids multiple times, the aforementioned process steps are performed again subsequent to the last step of regenerating the sensor and/or the sensor surface. The apparatus of the invention can thus perform the next analysis of fluid samples. Essential parts of the apparatus can thereby advantageously be used several times, such as the sensor, since regeneration of the sensor or the sensor surface ensures that the sensor surface is cleaned and that optionally the sensor surface is calibrated. After all the cavities arranged in the carrier tape have been used, the carrier tape, optionally with a cassette on which or in which the carrier tape is guided, needs to be replaced. Therefore, it is not necessary to clean any component of a respective measuring cell formed by the carrier tape, because the respective cavity is used only once. By arranging a plurality of cavities in the carrier tape and by being able to exchange the carrier tape, major components of the inventive apparatus can be used several times without risking that the results of the measurement and analysis are adversely affected.

In the method for analyzing fluid samples according to the invention, the sensor surface is contacted with the regeneration agent by opening a void in the carrier tape containing the regeneration agent.

Opening the void may in particular be realized by opening a rated break point, optionally by increasing a mechanical stress in the carrier tape in the region of the void.

To this end, mechanical pressure can be applied to the void. In an alternative embodiment, or optionally as an added feature to the rated break point, at least one void may be delimited on the side facing the sensor surface by a membrane or a film. By selecting the mechanical strength of such a membrane or of such film so that it is lower than the mechanical strength of the carrier tape, the film or membrane may yield and tear in particular under an increased mechanical stress, so that the regeneration agent is applied to the sensor surface. In a simple embodiment of the carrier tape, the carrier tape is provided on its entire surface on the side facing the sensor with such a membrane or such a film, in which a rated break point can optionally also be arranged.

As already mentioned with respect to apparatus of the invention, regeneration of the sensor of the sensor may include treatment of the sensor with detergents and/or treatment with a calibration agent. The sensor is thus also regenerated by treating the surface of the sensor.

According to a particularly advantageous embodiment, the sensor is treated with a detergent subsequent to the measurement or analysis of the sample fluid, followed by a treatment of the sensor with a calibration agent. Optionally, intermediate steps may be performed between the two aforementioned processes.

To avoid subsequent measurements and analyses from being false, the sensor, subsequent to the treatment of the sensor with the calibration agent, may be treated again at least once with a detergent. Optionally, the sensor may be calibrated several times with different calibration agents, as well as cleaned with different detergents.

With the apparatus according to the invention, the method according to the invention may therefore be used for examining and/or measuring and/or analyzing blood samples. To this end, a drop of blood, which is formed on a body part of a patient by, for example, using a lancing apparatus which is also included with the apparatus, is to be transferred into a cavity by capillary forces formed between the support tape and the sensor surface. The sensor can perform measurements, such as measurements of glucose, through the sensor surface by using appropriate biosensors and/or may further analyze the blood sample. The carrier tape is advanced automatically after completing the measurement and analyses, thereby forming a void above the sensor surface, in which detergent is contained. The void is opened due to increased mechanical stress, causing the detergent to be incident on the sensor surface and to perform a cleaning process. Thereafter, the carrier tape is moved onward, forming a void filled with a calibration agent above the sensor surface. This cavity is also opened due to the increased mechanical stress, causing the calibration agent to be incident on the sensor surface of the sensor, so that an automatic calibration can be performed. Thereafter, an already described washing process of the sensor surface can be follow by supplying the detergent to another cavity. After completion of the operations providing renewed operational readiness, the carrier tape preferably remains in a position wherein an open void with detergent is arranged on the sensor surface, thereby preventing the sensor surface from becoming contaminated or drying out when the apparatus according to the invention is not in use. In this state, the apparatus may turn off automatically or go into a standby mode. If a new measurement is desired, this should be entered in the apparatus by entering an activation command, e.g. by pressing a button on the apparatus, causing the carrier tape to move back into a position where a subsequent cavity for receiving sample fluid is located above the sensor surface. The measuring and analysis procedure can then be repeated as described above.

Figure 2:
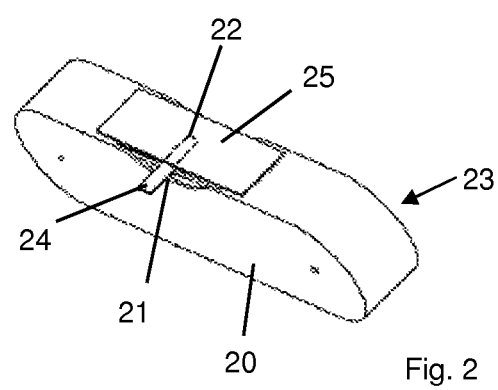
Figure 3:
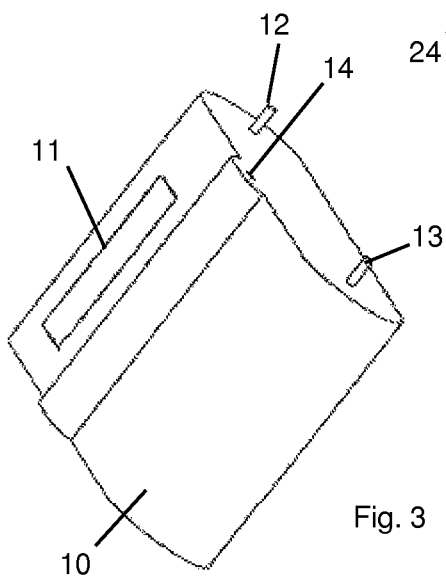
Figure 4:
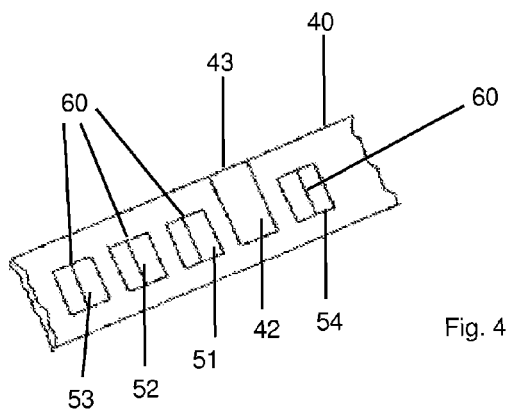
Figure 5:
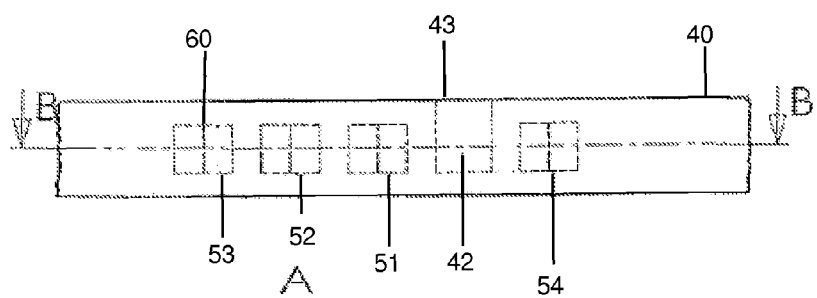
Figure 6:
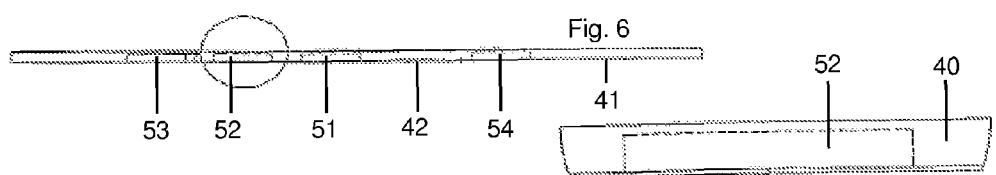
Figure 7:
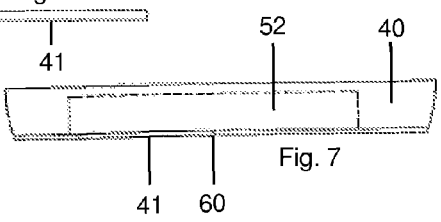
Figure 8:
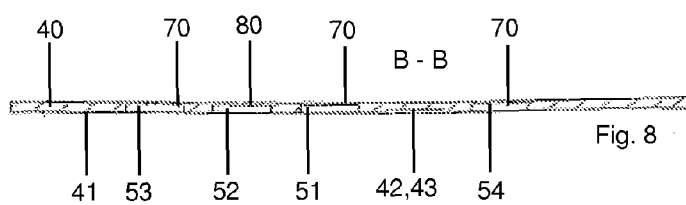

The present invention is described below with reference to exemplary embodiments illustrated in the accompanying drawings, which show in:

FIG. 1 an apparatus according to the invention in a perspective view,

FIG. 2 a cassette of the apparatus according to the invention in a perspective view, FIG. 3 a housing of the apparatus according to the invention in a perspective view, FIG. 4 a section of the carrier tape in a perspective view, FIG. 5 a section of the carrier tape in plan view, FIG. 6 a section of the carrier tape in a side view, FIG. 7 the detail A of FIG. 6 is an enlarged view, and FIG. 8 a sectional view B-B taken along the cross-sectional course indicated in FIG. 5.

As seen in particular from FIG. 1, the apparatus according to the invention is designed to be relatively compact and comfortable to handle, so that it is well equipped for mobile use and for operation by a patient. The apparatus includes a housing 10 in which a display 11 for displaying the measurement or analysis results is arranged. A cartridge 20, on which the carrier tape 40 can circulate, is connected laterally on the housing 10, as indicated by dashed line in FIG. 1. The present invention is not limited to an embodiment wherein the support tape 40 circulates in accordance with the approximate elliptic shape of the cassette 20; instead, the carrier tape 40 may be guided through the cassette 20 in several loops, allowing a significantly longer carrier tape to be employed. The sensor 21 is arranged inside the cartridge 20, or projecting into the cartridge 20, wherein the sensor surface 22 extends at least partially below a plate 25 and faces the carrier tape 40. In other words, the carrier tape 40 is guided above the sensor surface 22. The plate 25 can thereby be constructed so as to guide the carrier tape 40 and/or to apply pressure to the carrier tape 40. Several cavities 42 are arranged in the carrier tape 40, with only one cavity 42 being illustrated in FIG. 1. The measuring cell 30 is defined, on one hand, by the cavity 42 and, on the other hand, by the sensor surface 22. This cavity 42, also shown by dashed lines, has a lateral opening 43 arranged on the side facing away from the housing 10 for receiving sample fluid 44. The sample fluid thereby reaches the sensor surface 22, allowing the sensor 21 to perform the necessary measurements and analyses. Voids 51 to 54 are arranged next to the cavity 42. These voids 51 to 54 contain regeneration agents, as will be further described below.

The sensor 21 may be built into the cartridge 20, or may also be rigidly connected to the housing 10 and only partially penetrate the cassette 20. The cartridge 20 may be configured as a single-use unit in which the carrier tape 40 is received so that the entire cartridge and thus also the carrier tape 40 must be replaced when all cavities 42 of the carrier tape 40 have been used. If the sensor 21 is also a component of the cartridge 20, then it must also be exchanged and replaced with a new cartridge 20 including a sensor 21. However, if the sensor 21 is a component that is fixedly connected to the housing 10, the sensor 21 is not exchanged when replacing the cassette 20.

To implement the measurement and analyses operations and the movements of the carrier tape, the apparatus of the invention may include an unillustrated control or regulating device and an energy storage device, for example in the form of at least one battery.

As seen in FIG. 2, the cartridge 20 is a separate component that can be separated from the housing shown in FIG. 3. For transmitting data and/or for supplying power, at least one contact 24 (not shown in detail) is arranged on the sensor 21 between the cassette 20 and the housing 10, wherein the sensor may particularly be a reusable biosensor.

As is apparent in particular from FIG. 3, at least one drive shaft 12 is disposed in the housing which can be used to drive a drive and positioning system 23, which is part of cartridge 20. Stated differently, a drive unit in the housing is controlled by a suitable control or regulating device, which transmits a corresponding torque via the drive shaft 12 to the drive and positioning system 23 for moving and positioning the carrier tape 40 in the desired manner. Since the cartridge 20 and the drive and positioning system 23 are advantageously configured such that the carrier tape is guided over two deflection rollers, an axis 13 enabling rotation of the guide wheels is also provided on the housing.

As mentioned above, the entire cartridge 20 can be exchanged, wherein when a new cartridge 20 is arranged on the housing 10, the contact 24 on the sensor 21 is to be inserted into the bushing 14 on the housing 10.

FIGS. 4 to 8 show a detail of the carrier tape, which circulates on the cartridge or in the cartridge 20. As seen in FIG. 4, the carrier tape has a relatively small thickness and has a cavity 42 with a lateral opening 43 on one side. This cavity serves to hold the sample fluid 44, such as blood. A first void 51 is disposed adjacent to the cavity 42, a second void 52 is disposed next to this first void 51, and a third void 53 is disposed next to the second void 52. A fourth void 54 is arranged on the side opposite the first void 51. Each of the cavities 51 to 54 has a rated break point 60; however, the invention is not limited to the formation of a rated break point; instead, other suitable embodiments of the carrier tape 40 may be provided which permit the respective void to open.

As illustrated in particular in FIG. 6, the cavity 42 has a relatively small height, so that, for example, blood can be received in the cavity 42 through the side opening 43 due to capillary action. The voids 51 to 54 arranged next to the cavity 42 have a greater height for the purpose of accommodating a corresponding volume of regeneration agents. The heights of the cavities 51 to 54 and of the cavity 42 are clearly visible in FIG. 8.

As shown in the detail A in FIG. 7, the carrier tape 40 may include on its underside a membrane 41, which may optionally also have the illustrated rated break point 60. When a sufficiently large force is applied to the void 52, the void 52 opens at the rated break point, thus allowing the regeneration agent received in the void 52 to flow through the rated break point 60 and then reaching the sensor surface 22. The carrier tape has on its bottom a membrane 41 or a film which can be used to seal several voids and which may optionally break due to the increased mechanical stress, thereby releasing the particular regeneration agent.

According to a particular embodiment, a 70 detergent is received in the first void 51, and a calibration agent is received in the second void 52, and a detergent is also received in the third and fourth voids 53 and 54, respectively. With this arrangement and when the carrier tape 40 is moved in one direction, the first void 51 moved above the sensor surface 22 after receiving sample fluid in the cavity 42 and subsequent to the measurement and analysis, wherein detergent 70 contained in this void 51 is applied to the sensor surface for cleaning the sensor surface 22. Thereafter, the carrier tape is moved so that the second void 52 is located above the sensor surface, causing calibration agent 80 to be released onto the sensor surface, thereby calibrating the sensor. Thereafter, the third void 53 is positioned above the sensor surface 22, which also supplies detergent to the sensor surface. For re-cleaning and also for protecting against ambient effects, the carrier tape is moved so that a fourth void 54 is placed above the sensor surface 22, which supplies the corresponding detergent to the sensor surface 22. The fourth void 54 is shown in FIGS. 4 to 8 on the right-hand side of the cavity 42. However, this does not mean that the transport direction of the carrier tape must be changed, but only that the fourth void 54 is disposed a relatively close distance before the next cavity that receives the sample fluid. After the measurement and analysis have been performed, the apparatus of the invention stops the feed operation of the carrier tape 40 at the position where the fourth void 54 is disposed above the sensor surface, thereby permanently protecting the sensor surface from contamination and/or from drying out.

At a restart of the inventive apparatus to perform a new measurement, the carrier tape 40 is automatically brought into a position where, as shown in FIG. 1, a previously unused cavity 42 is disposed above the sensor surface 22 for the purpose of receiving new sample fluid.

It is apparent that the inventive apparatus and method of the invention can be employed easily, reliable and self-explanatory without the need to move or pump fluid flows and without the risk of adversely affecting the measurement or analysis. Thus, a relatively high-quality diagnosis and monitoring of patients, especially diabetic patients, can be performed by the patient's themselves and decentralized, allowing improved patient care via communication networks. It is expected that despite the relatively low technical complexity of the apparatus according to the invention as well as thanks to the ease of its use, diagnostic and monitoring can be performed more reliably and more accurately, which may significantly reduce the severity of secondary illnesses.

List of Reference Numerals
Housing 10
Display 11
Drive shaft 12
Axis 13
Bushing 14
Cassette 20
Sensor 21
Sensor surface 22
Drive and positioning system 23
Contact 24
Plate 25
Measuring cell 30
Carrier tape 40
Membrane 41
Cavity 42
Lateral opening 43
Sample fluid 44
First cavity 51
Second cavity 52
Third cavity 53
Fourth cavity 54
Rated break point 60
Detergent 70
Calibration agent 80

The invention claimed is:

1. An apparatus for analyzing sample fluids, comprising a sensor for measuring at least one value of a sample fluid, wherein the sensor has a sensor surface via which the measurement can be undertaken, the apparatus further comprising a carrier tape, with which in cooperation with the sensor surface at least one measuring cell for receiving sample fluid is formed between the sensor surface and a pocket or cavity formed in the carrier tape that has a small depth and hollow volume, wherein the depth and volume are dimensioned such that capillary forces alone are sufficient to draw the sample fluid into the pocket or cavity, further in addition to the pocket or cavity on the carrier tape, at least one regeneration agent for regenerating the sensor is contained in at least one void in the carrier tape, wherein the carrier tape is movable and configured such that the regeneration agent from the void can be applied on the sensor surface after the measurement has taken place.

2. The apparatus for analyzing fluid samples according to claim 1, wherein detergents and/or calibrating agents as regeneration agents are contained in several voids in the carrier tape.

3. The apparatus for analyzing fluid samples according to claim 1, wherein the carrier tape is an endless tape or disk.

4. The apparatus for analyzing fluid samples according to claim 1, wherein the apparatus comprises a drive and positioning system for transporting and sequentially positioning the respective cavities for receiving the sample fluid and the voids with regeneration agents above the sensor surface.

5. The apparatus for analyzing fluid samples according to claim 1, wherein the apparatus comprises a pressure device for applying mechanical pressure to a respective void provided with a regeneration agent.

6. The apparatus for analyzing fluid samples according to claim 1, wherein the cavity for receiving the sample fluid is substantially open on a side facing the sensor surface.

7. A method for analyzing sample fluids, wherein at least one value of a sample fluid is measured by a sensor, the method comprising the steps of:
 a) Positioning a cavity delimited by a carrier tape above a sensor surface, wherein the cavity is formed in the carrier tape and has a small depth and hollow volume, wherein the depth and volume are dimensioned such that capillary forces alone are sufficient to draw a sample fluid into the cavity,
 b) Receiving sample fluid in the cavity,
 c) Measuring at least one value of the sample fluid,
 d) Removing the cavity together with the sample fluid from the sensor surface,
 e) Supplying a regeneration agent to the sensor surface by way of the carrier tape,
 f) Contacting the sensor surface with the regeneration agent for regenerating the sensor, and at which the sensor surface is contacted with the regeneration agent by opening a void in the carrier tape in which the regeneration agent resides.

8. The method for analyzing sample fluids according to claim 7, wherein the void containing the regeneration agent is opened by opening a rated break point.

9. The method for analyzing fluid samples according to claim 7, wherein mechanical pressure is applied to the void in order to open the void.

10. The method for analyzing fluid samples according to claim 7, wherein regeneration of the sensor comprises a treatment of the sensor with detergent and/or a treatment of the sensor with a calibration agent.

11. The method for analyzing sample fluids according to claim 10, wherein after the measurement the sensor is treated with a detergent, followed by treatment of the sensor with a calibration agent.

12. The method for analyzing sample fluids according to claim 11, wherein after the sensor has been treated with the calibration agent, the sensor is treated again at least once with a detergent.

* * * * *